(12) United States Patent
Joo

(10) Patent No.: US 12,402,930 B2
(45) Date of Patent: Sep. 2, 2025

(54) BONE TUMOR SURGERY DEVICE

(71) Applicant: THE CATHOLIC UNIVERSITY OF KOREA INDUSTRY-ACADEMIC COOPERATION FOUNDATION, Seoul (KR)

(72) Inventor: Min Wook Joo, Suwon-si (KR)

(73) Assignee: THE CATHOLIC UNIVERSITY OF KOREA INDUSTRY-ACADEMIC COOPERATION FOUNDATION, Seoul (KR)

(*) Notice: Subject to any disclaimer, the term of this patent is extended or adjusted under 35 U.S.C. 154(b) by 636 days.

(21) Appl. No.: 17/784,193

(22) PCT Filed: Dec. 8, 2020

(86) PCT No.: PCT/KR2020/017871
§ 371 (c)(1),
(2) Date: Jun. 10, 2022

(87) PCT Pub. No.: WO2021/118207
PCT Pub. Date: Jun. 17, 2021

(65) Prior Publication Data
US 2023/0022039 A1    Jan. 26, 2023

(30) Foreign Application Priority Data
Dec. 10, 2019   (KR) ........................ 10-2019-0163723

(51) Int. Cl.
*A61B 18/14* (2006.01)
*A61B 18/12* (2006.01)
*A61B 18/00* (2006.01)

(52) U.S. Cl.
CPC .......... *A61B 18/1206* (2013.01); *A61B 18/14* (2013.01); *A61B 2018/00011* (2013.01); *A61B 2018/00565* (2013.01)

(58) Field of Classification Search
CPC ..... A61B 18/12; A61B 18/1206; A61B 18/14; A61B 2018/00011; A61B 2018/00017;
(Continued)

(56) References Cited
U.S. PATENT DOCUMENTS 4,462,412 A * 7/1984 Turner ................... A61N 1/403
607/98
7,799,024 B2 * 9/2010 Randall .............. A61B 18/1477
606/41
(Continued)

FOREIGN PATENT DOCUMENTS

KR         20-0264071       10/2001
KR     10-2011-0002048       1/2011
(Continued)

OTHER PUBLICATIONS

Habash et al. "Thermal Therapy, Part 2: Hyperthermia Techniques.", *Critical Reviews in Biomedical Engineering*, 34(6): 501-511, 2006.
(Continued)

*Primary Examiner* — Michael F Peffley
(74) *Attorney, Agent, or Firm* — NORTON ROSE FULBRIGHT US LLP

(57) ABSTRACT

A bone tumor surgery device according to an embodiment of the present invention comprises: an accommodation container in which an accommodation space for accommodating a bone of a patient is formed; and a radiofrequency supply unit for supplying radiofrequency into the accommodation space.

9 Claims, 4 Drawing Sheets

(58) Field of Classification Search
CPC ........... A61B 2018/00035; A61B 2018/00565; A61B 2018/00577; A61B 2018/00595; A61B 2018/142

See application file for complete search history.

(56) References Cited

U.S. PATENT DOCUMENTS

| | | | | |
|---|---|---|---|---|
| 2004/0044385 | A1* | 3/2004 | Fenn | A61N 1/403 607/100 |
| 2004/0059328 | A1* | 3/2004 | Daniel | A61B 18/1477 606/41 |
| 2012/0290049 | A1* | 11/2012 | Marc | A61N 1/403 607/98 |
| 2017/0049503 | A1* | 2/2017 | Cosman | A61B 18/1477 |
| 2018/0014871 | A1* | 1/2018 | Mitra | A61M 37/00 |

FOREIGN PATENT DOCUMENTS

| | | |
|---|---|---|
| KR | 10-1021050 | 3/2011 |
| KR | 10-2015-0046510 | 4/2015 |

OTHER PUBLICATIONS

International Search Report issued in corresponding PCT Application No. PCT/KR2020/017871, dated Mar. 24, 2021 (English Translation).

Written Opinion issued in corresponding PCT Application No. PCT/KR2020/017871, dated Mar. 24, 2021 (Korean).

\* cited by examiner

BONE TUMOR SURGERY DEVICE

CROSS-REFERENCE TO RELATED APPLICATIONS

This application is a national phase application under 35 U.S.C. § 371 of International Application No. PCT/KR2020/017871, filed Dec. 8, 2020, which claims priority to and the benefit of Korean Application No. 10-2019-0163723, filed Dec. 10, 2019. The contents of the referenced patent applications are incorporated into the present application by reference.

TECHNICAL FIELD

The present invention relates to a bone tumor surgery device, and more particularly, to a bone tumor surgery device that can be applied to a limb salvage operation among surgical treatment of musculoskeletal tumors.

BACKGROUND

From several decades to the present, wide resection and reconstruction have been considered the standard of limb salvage operation in the surgical treatment of musculoskeletal tumors. That is, the methods of reconstructing the bone defect through tumor-prosthesis, allograft, and recycled autograft after wide resection of the patient's bone where the tumor exists is widely used. However, this method is pointed out as a problem in bone loss due to wide resection of the lesion, and the possibility of graft fracture and infection, etc.

Meanwhile, pedicle frozen autograft surgery is sometimes used to overcome the disadvantages of recycled autograft among the above methods. The pedicle frozen autograft surgery is performed in a way that after performing osteotomy only in the metaphysis of the long tubular bone with a relatively good union rate, the tumor outside the bone and inside the medullary cavity is removed, then the part containing the tumor is moved out from the surgical field, and then freeze and thaw treatment is repeated.

However, in the pedicle frozen autograft surgery, there are problems such as a possibility of contamination of the surgical area by tumor cells during the removal of tumors outside the bone and inside the medullary cavity; the risk of the operator having to hold the limb for a long time after by oneself lifting the limb and putting it in the liquid nitrogen container; and the non-uniformity of the bone cooling temperature.

In such a situation, in order to minimize bone resection and preserve the patient's bones as much as possible, a tumor surgery technique using microwave is also being introduced. This is based on the fact that tumor cells die at a certain temperature range.

However, conventional surgical devices using microwave employ catheters, coaxial antennas, etc., it is practically difficult to apply to a wide range of tumor removal because microwave is irradiated limitedly to the patient's bone by using such devices, and even if multiple devices are used, it is impossible to determine the device insertion density for uniform temperature transfer. In addition, it is impossible to safely collect live tumor cells from within the surgical field prior to insertion of the microwave surgical device, making pathological determination of the tumor impossible.

Accordingly, it is required for the development of new technologies for limb salvage operation through which stable operation is possible through application within the surgical field, live tumors can be safely removed and har-vested without the possibility of tumor contamination, and complete tumor death is possible by consistently delivering the targeted temperature.

SUMMARY OF THE INVENTION

Technical Problem

The present invention is directed to providing a bone tumor surgery device capable of stably removing a tumor without the possibility of contamination in a surgical field without wide bone resection.

In addition, the present invention is directed to providing a bone tumor surgery device that effectively transfers heat for killing bone tumors to a patient's bone.

Technical Solution

In an aspect, the present invention provides a bone tumor surgery device comprising an accommodation container in which an accommodation space for accommodating a bone of a patient is formed; and a radiofrequency supply unit for supplying radiofrequency into the accommodation space.

In this case, the radiofrequency supply unit may include a radiofrequency generator; a heating electrode coupled to the accommodation container for transmitting the radiofrequency generated by the radiofrequency generator into the accommodation space; and a cable connecting the radiofrequency generator and the heating electrode.

In addition, the cable may be a coaxial cable including a center conductor, and an outer conductor insulated from the center conductor and disposed to surround the center conductor; the center conductor may be connected to the heating electrode; and the outer conductor may be connected to the accommodation container.

In addition, the bone tumor surgery device may further include a cooling fluid supply unit for supplying cooling fluid into the accommodation space.

In addition, the cooling fluid supply unit may include an inlet conduit for supplying the cooling fluid and a supply conduit connected to the inlet conduit and disposed in the accommodation space.

In addition, the supply conduit may have one or more outlets formed along its longitudinal direction so that the cooling fluid is discharged into the accommodation.

In addition, the accommodation space may be formed in a cylindrical shape.

In addition, the accommodation container may include a lower container forming a lower portion of the accommodation space and an upper container coupled to the lower container and forming an upper portion of the accommodation space.

In addition, the accommodation container may include a window formed to allow the accommodation space to be observed from the outside.

In addition, the accommodation container may include an insertion hole formed through one side thereof to insert the bone into the accommodation space.

According to the bone tumor surgery device according to an embodiment of the present invention, it is possible to efficiently and completely remove a bone tumor by irradiating radiofrequency to the patient's bone disposed in the accommodation space of the accommodation container.

In addition, according to the bone tumor surgery device according to an embodiment of the present invention, through efficient heat treatment using radiofrequency, surgical treatment of bone tumors can be achieved without wide bone resection, reconstruction using tumor-prosthesis or allograft.

BRIEF DESCRIPTION OF THE DRAWINGS

The above and other aspects, features, and advantages of the present invention will become more apparent to those of ordinary skill in the art by describing embodiments thereof in detail with reference to the accompanying drawings, in which.

DETAILED DESCRIPTION OF THE EMBODIMENTS

Figure 1:
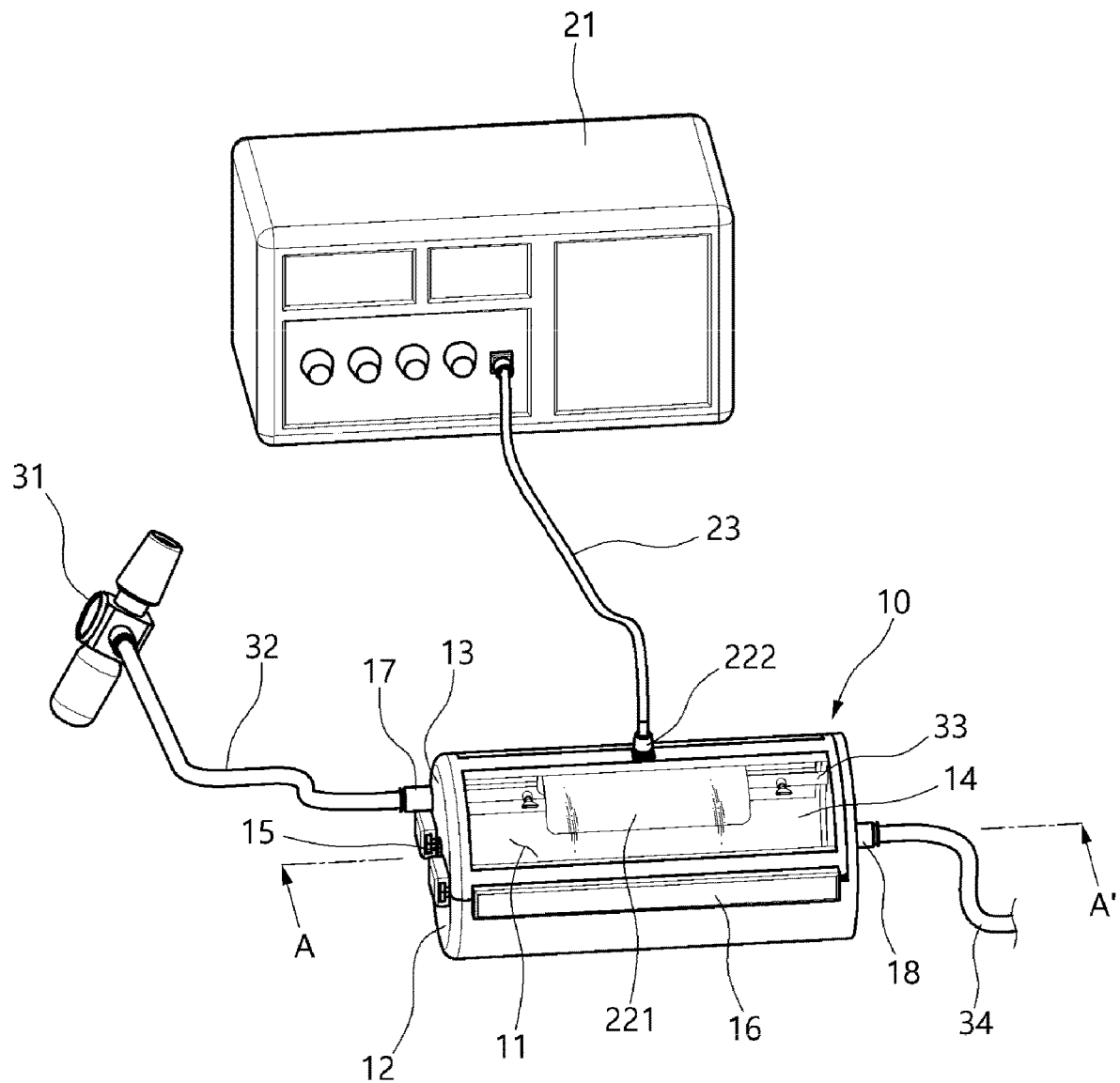
FIG. 1 is a view showing a bone tumor surgery device according to an exemplary embodiment of the present invention.

Hereinafter, exemplary embodiments of the present invention will be described in detail so that those of ordinary skill in the art can readily implement the present invention with reference to the accompanying drawings. The present invention may be embodied in many different forms and are not limited to the embodiments set forth herein. In the drawings, parts unrelated to the description are omitted for clarity. Throughout the specification, like reference numerals denote like elements.

It is understood that the terms "comprise" or "have" when used in this specification, are intended to describe the presence of stated features, integers, steps, operations, members, components and/or a combination thereof but not preclude the possibility of the presence or addition of one or more other features, integers, steps, operations, members, components, or a combination thereof.

In addition, in this specification, spatially relative terms "front", "rear", "upper or above or top" or "lower or below or bottom" may be used to describe a correlation with the elements shown in the drawings. These are relative terms determined based on what is shown in the drawings, and the positional relationship may be conversely interpreted according to the orientation.

In addition, the presence of an element in/on "front", "behind", "above" or "below" of another element includes not only being disposed in/on "front", "rear", "above" or "below" directly in contact with other elements, but also cases in which another element being disposed in the middle, unless otherwise specified.

Figure 2:
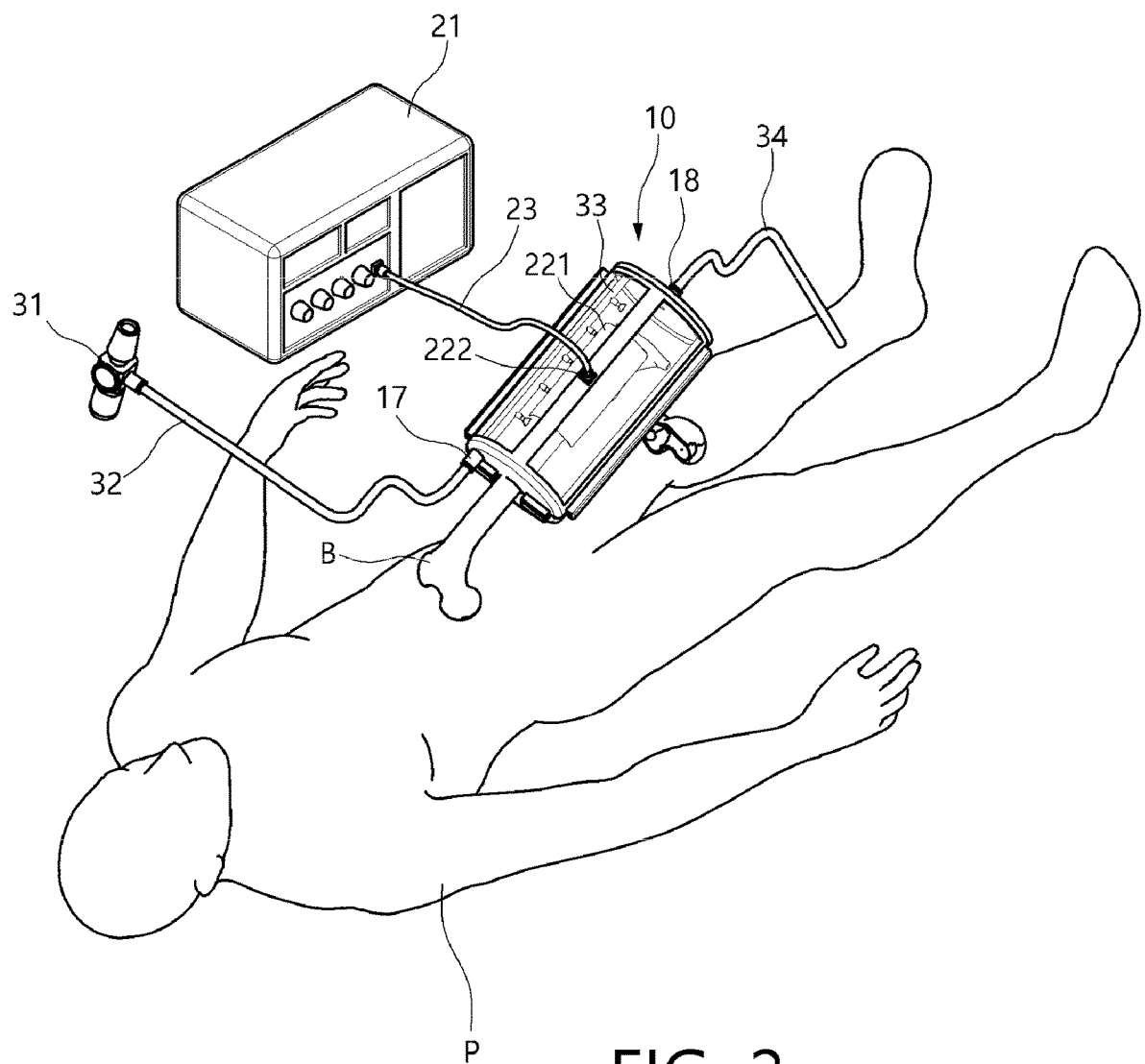
FIG. 2 is a view showing a state of usage of the bone tumor surgery device according to an exemplary embodiment of the present invention.
Figure 3:
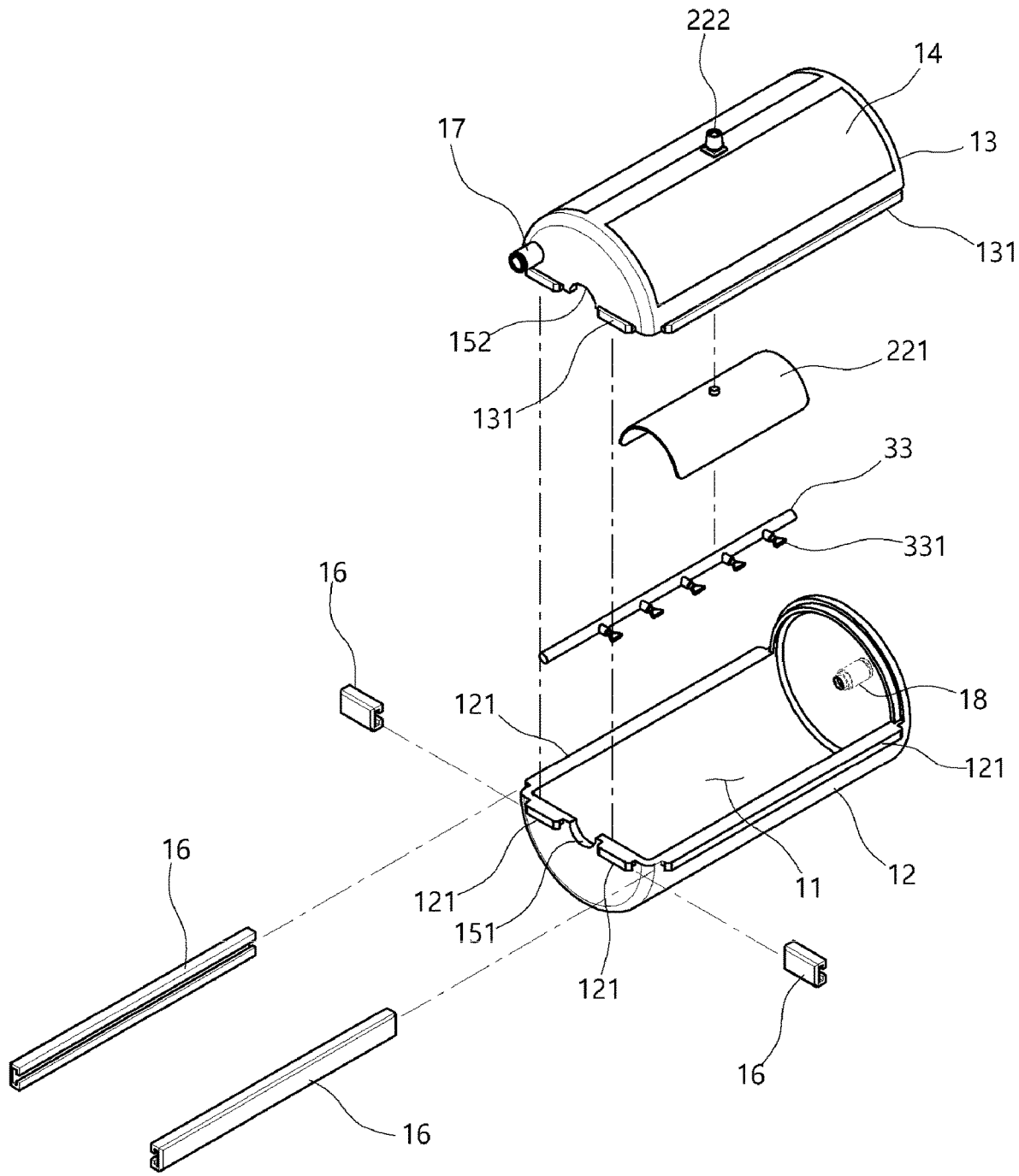
FIG. 3 is an exploded view of an accommodation container part of the bone tumor surgery device according to an exemplary embodiment of the present invention.
Figure 4:
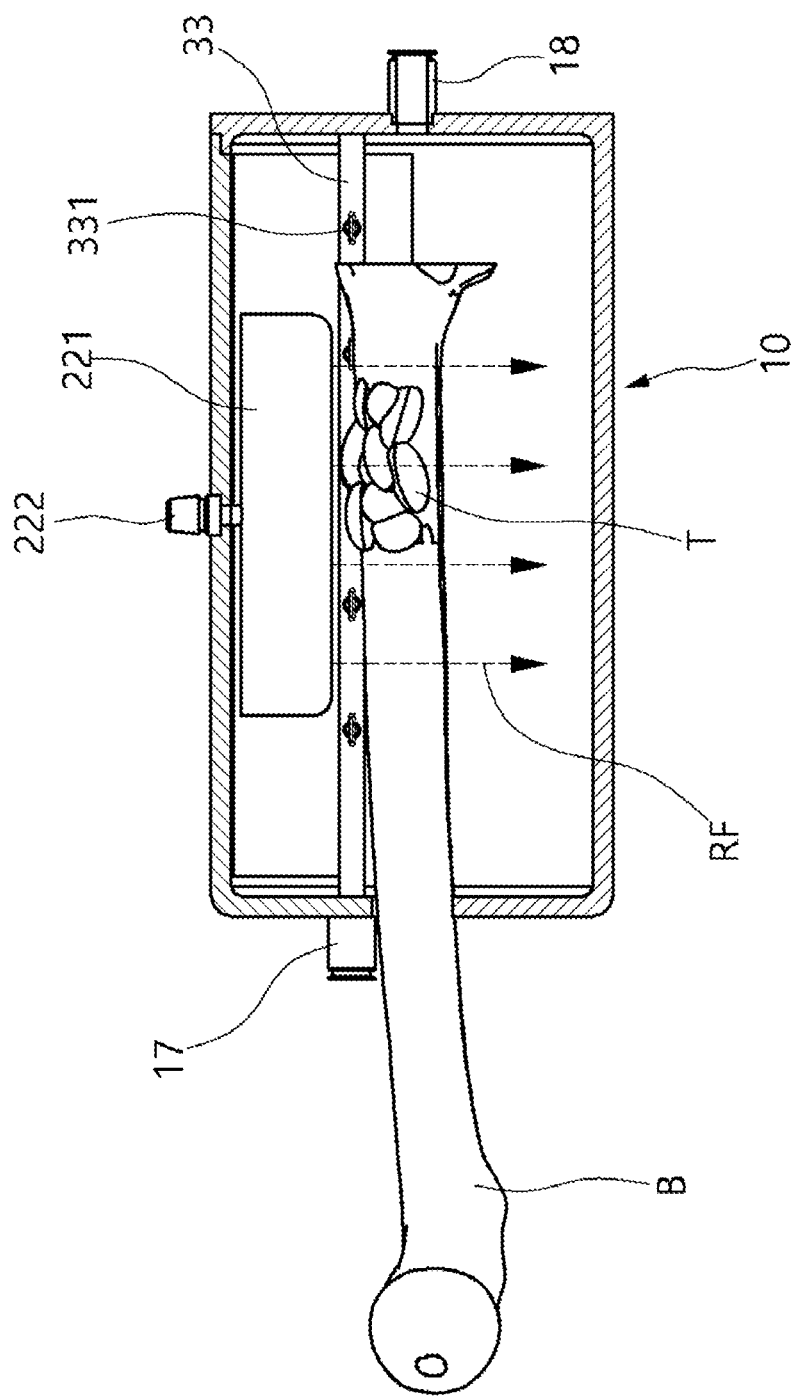
FIG. 4 is a view showing the accommodation container into which the patient's bones are inserted, taken along section A-A' of FIG. 1.

FIG. 1 is a view showing a bone tumor surgery device according to an exemplary embodiment of the present invention; FIG. 2 is a view showing a state of usage of a bone tumor surgery device according to an exemplary embodiment of the present invention. In addition, FIG. 3 is an exploded view of an accommodation container part of the bone tumor surgery device according to an exemplary embodiment of the present invention. FIG. 4 is a view showing the accommodation container into which the patient's bones are inserted, taken along section A-A' of FIG. 1.

A bone tumor surgery device according to an embodiment of the present invention allows to kill the tumor T using radiofrequency in a state that accommodates the bone B of the patient P in the accommodation container 10, and to reuse the patient's own bone B as much as possible. Specifically, as shown in FIG. 2, in case the bone tumor surgery device according to an embodiment of the present invention is applied to long tubular bone containing a tumor, it is possible to kill tumor cells in situ through radiofrequency after resection of the metaphysis or epiphysis of the long tubular bone (the other side of the long tubular bone is not resected). According to an embodiment of the present invention, a patient can maintain a highly durable limb for a long time through a simple operation.

Referring to FIGS. 1 to 4, the bone tumor surgery device according to an embodiment of the present invention may include an accommodation container 10, a radiofrequency supply unit 20, and a cooling fluid supply unit 30.

The accommodation container 10 provides an accommodating space 11 for accommodating the bone B of the patient P. The accommodation space 11 is a portion for accommodating the bone B of the patient P in the accommodation container 10. According to an embodiment of the present invention, the accommodating space 11 is formed in the accommodating container 10 in a state in which a lower container 12 and an upper container 13 are coupled. A radiofrequency (RF) is transmitted to the bone B of the patient P disposed in the accommodation space (11), and heat treatment for the death of the tumor cells T is performed.

The accommodation container 10 is preferably made of a material or structure having dielectric properties that can block the radiofrequency in the accommodation space 11 from leaking to the outside. That is, it is preferable that the material of the accommodation container 10 can be insulated and shielded. In addition, the accommodation container 10 may be made of a material that can be sterilized.

As an example of a material that satisfies the above characteristics, a metal plate, a metal mesh structure, or a plastic material or the like may be used. More specifically, stainless steel, aluminum, or the like may be used.

As best shown in FIG. 3, in an embodiment of the present invention, the accommodation container 10 may include a lower container 12 forming a lower portion of the accommodation space 11 and an upper container 13 coupled to the lower container 12 and forming an upper portion of the accommodation space 11. More specifically, the lower container 12 and the upper container 13 may form a cylindrical shape in the coupled state and form a cylindrical accommodation space 11 therein.

The lower container 12 is formed in a semi-cylindrical shape with an open-top. A first protrusion 121 is formed in at least a portion of the lower container 12 in contact with the upper container 13. The first protrusion 121 is a portion to which a fastening part 16 to be described later is coupled for stable coupling of the lower container 12 and the upper container 13. The first protrusion 121 may protrude outward by a predetermined length from the outer surface of the lower container 12, and the outer end thereof may additionally protrude downward so that the transverse section thereof may have a shape such as '¬'.

The upper container 13 is formed with an open bottom so as to cover the open portion of the lower container 12. That is, the upper container 13 may have a cover shape that covers the open portion of the lower container 12.

A second protrusion 131 is formed in a portion of the upper container 13 in contact with the first protrusion 121 of the lower container 12. The second protrusion 131 is a portion to which a fastening part 16 to be described later is coupled for stable coupling of the lower container 12 and the upper container 13. Specifically, the second protrusion 131 may protrude outward by a predetermined length from the outer surface of the upper container 13, and the outer end thereof may additionally protrude upward so that the transverse section thereof may have a shape such as '|'.

Further, in an embodiment of the present invention, the accommodation container 10 includes a window 14 that allows the accommodation space 11 to be observed from the outside. Specifically, according to an embodiment of the present invention, the window 14 is formed on the upper container 13. The surgeon performing the operation may visually check the bone B of the patient P disposed in the accommodation space 11 through the window 14.

In addition, an insertion hole 15 for inserting the bone B of the patient P into the accommodation space 11 may be formed on one side of the accommodation space 11 of the accommodation container 10. In this case, a sealing member (not shown) made of a material considering the protection of the bone B and prevention of radiofrequency leakage may be coupled to the insertion hole 15 in contact with the bone B of the patient P. For example, the sealing member may be a ring-shaped member made of a soft material to be fitted into the insertion hole.

In an embodiment of the present invention, the lower container 12 and the upper container 13 form an insertion hole 15 in the coupled state. To this end, the lower container 12 includes a first invagination portion 151 invaginated downward into one wall in the longitudinal direction, and the upper container 13 includes a second invagination portion 152 invaginated upward into a portion of one wall in the longitudinal direction in contact with the first invagination portion 151 of the lower container 12. When the lower container 12 and the upper container 13 are coupled, the first invagination portion 151 and the second invagination portion 152 form one insertion hole 15. The combination of the lower container 12 and the upper container 13 can be made in a state in which the patient's bone B is placed in the accommodation space 11 of the accommodation container 10 through the insertion hole 15 formed in this way.

The fastening part 16 fastens the coupling portion of the lower container 12 and the upper container 13. Through the fastening part 16, the lower container 12 and the upper container 13 can maintain a stable fastening state.

As described above, in an embodiment of the present invention, the lower container 12 and the upper container 13 include the first protrusion 121 and the second protrusion 131, respectively. In this regard, the fastening part 16 may be a length member (e.g., a sleeve) that surrounds and couples the first protrusion 121 and the second protrusion 131 together.

More specifically, in an embodiment of the present invention, in a state in which the lower container 12 is covered by the upper container 13, the first protrusion 121 and the second protrusion 131 come into contact and protrude outward by a predetermined length from the outer surface of the housing 10, the outer end thereof is additionally protruded upward and downward so that its transverse section appears as '⊣'. Accordingly, the fastening part 16 may be made of a length member that is fitted while surrounding the abutting first protrusion 121 and second protrusion 131 and whose longitudinal cross-section appears in a shape complementary to '⊣'.

In addition, the fastening part 16 may include a metal slit for preventing the radiofrequency and heat from leaking from the accommodation space 11. More specifically, when the fastening part 16 is formed of a length member, a plurality of metal slits may be formed along the longitudinal direction of the fastening part 16.

The radiofrequency supply unit 20 supplies a radiofrequency into the accommodation space 11. In an embodiment of the present invention, the radiofrequency supply unit 20 may include a radiofrequency generator 21, a heating electrode 22 and a cable 23.

The radiofrequency generator 21 is a device for generating a radiofrequency that can heat the bone B of the patient P disposed in the accommodation space 11. The radiofrequency generator 21 may receive power to generate a radiofrequency, match the generated radiofrequency and output it. The radiofrequency output from the radiofrequency generator 21 may be, for example, 25 to 30 MHz. More specifically, the radiofrequency may be 27.12 MHz. Of course, the range of the radiofrequency output from the radiofrequency generator 21 is not limited thereby, and any radiofrequency capable of heating the deep part of the bone B of the patient P to an appropriate temperature may be selected.

In addition, the radiofrequency generator 21 may be configured to generate a radiofrequency in a specific range, but configured to be capable of setting power, time, and the like differently as needed. To this end, the radiofrequency generator 21 may provide an interface (e.g., a button, a knob, a touch-type display, etc.) capable of setting power, time, and the like.

The heating electrode 22 transmits a radiofrequency into the accommodation space 11. In an embodiment of the present invention, the heating electrode 22 includes an electrode body 221 and a connector 222. The electrode body 221 is disposed in the accommodation space 11. The electrode body 221 may be formed of a plate material. For example, the electrode body 221 may be curved in an arc shape. In addition, the connector 222 may be electrically connected to the electrode body 221 so that the electrode body 221 can be connected to the radiofrequency generator 21, and may be provided outside the accommodation container 10.

The electrode body 221 may be disposed in an upper portion of the accommodation space 11. Specifically, in an embodiment of the present invention, the electrode body 221 may be coupled to the upper container 13. In addition, the electrode body 221 may be a first electrode (e.g., anode), and the lower portion of the container 10 may be a second electrode (e.g., cathode). Accordingly, the radiofrequency may be supplied to the bone B disposed between the electrode body 221 and the inner wall of the accommodation container 10 in the accommodation space 11.

The cable 23 connects the radiofrequency generator 21 and the heating electrode 22. In an embodiment of the present invention, the cable 23 may be a coaxial cable including a center conductor, and an outer conductor surrounding the center conductor in a state insulated from the center conductor by an insulator.

In this case, the center conductor of the cable 23 may be connected to the electrode body 221 and the outer conductor may be connected to the accommodation container 10, so that, as described above, a high frequency may be supplied to the bone B disposed between the electrode body 221 and the inner wall of the accommodation container 10 in the accommodation space 11.

The cooling fluid supply unit 30 supplies cooling fluid into the accommodation space 11. When the radiofrequency is transmitted to the bone B of the patient P disposed in the accommodation space 11, if the surface of the bone B is excessively heated, not only the tumor cells T but also normal cells may be damaged; the cooling fluid flows into the accommodation space 11 and acts to cool, thereby preventing local heating of the surface of the bone B. Through this, while avoiding excessive heating of the surface of the bone B through the radiofrequency, the radiofrequency may be sufficiently transmitted to the deep part of the bone B, so that it is possible to sufficiently heat the tumor cells in the deep part.

For example, the cooling fluid supplied by the cooling fluid supply unit 30 may be air. That is, in an embodiment of the present invention, the cooling fluid supply unit 30 may supply air into the accommodation space 11.

In an embodiment of the present invention, the cooling fluid supply unit 30 may include a pneumatic regulator 31 connected to an external air tank (not shown) to supply air at a constant pressure, an inlet conduit 32 connected between the pneumatic regulator 31 and the accommodation space 11, a supply conduit 33 connected to the inlet conduit 32 and disposed in the accommodation space 11, and an outlet conduit 34 connected to the outside in the accommodation space 11.

In this regard, the accommodation container 10 may include a cooling fluid inlet 17 formed through one side of the accommodation space 11 and a cooling fluid outlet 18 formed through the other side of the accommodation space 11. That is, the inlet conduit 32 may be connected to the cooling fluid inlet 17, and the outlet conduit 34 may be connected to the cooling fluid outlet 18.

In addition, the supply conduit 33 may have one or more outlets formed along its longitudinal direction so that the cooling fluid is discharged into the accommodation space 11. For example, the outlet may be formed of a through hole, a slit, or the like.

In an embodiment of the present invention, the supply conduit 33 communicates with the inlet conduit 32 and is disposed in the accommodation space 11, and by providing a plurality of outlets 331 in the form of discharge holes along the longitudinal direction thereof, allows the cooling fluid to be uniformly supplied into the accommodation space 11.

Although exemplary embodiments of the present disclosure have been described, the spirit of the present disclosure is not limited to the embodiments set forth herein. Those of ordinary skill in the art who understand the spirit of the present disclosure may easily propose other embodiments through supplement, change, removal, addition, etc. of elements within the same spirit, but the embodiments will be also within the scope of the present disclosure.

What is claimed is:

1. A bone tumor surgery device comprising:
an accommodation container in which an accommodation space for accommodating the bone of a patient is formed, the bone being exposed outside the patient's skin; and
a radiofrequency supply unit for supplying radiofrequency into the accommodation space,
wherein the accommodation container comprises an insertion hole formed through one side thereof to insert the bone into the accommodation space,
wherein the radiofrequency supply unit comprises a radiofrequency generator and a heating electrode coupled to the accommodation container for transmitting the radiofrequency generated by the radiofrequency generator into the accommodation space, and
wherein the heating electrode comprises an electrode body configured to be disposed in the accommodation space, the electrode body transmitting the radiofrequency to the bone disposed between the electrode body and an inner wall of the accommodation container.

2. The bone tumor surgery device of claim 1, wherein the radiofrequency supply unit further comprises a cable connecting the radiofrequency generator and the heating electrode.

3. The bone tumor surgery device of claim 2, wherein the cable is a coaxial cable including a center conductor, and an outer conductor insulated from the center conductor and disposed to surround the center conductor; the center conductor is connected to the heating electrode; and the outer conductor is connected to the accommodation container.

4. The bone tumor surgery device of claim 1, further comprising a cooling fluid supply unit for supplying cooling fluid into the accommodation space.

5. The bone tumor surgery device of claim 4, wherein the cooling fluid supply unit comprises an inlet conduit for supplying the cooling fluid and a supply conduit connected to the inlet conduit and disposed in the accommodation space.

6. The bone tumor surgery device of claim 5, wherein the supply conduit has one or more outlets formed along its longitudinal direction so that the cooling fluid is discharged into the accommodation space.

7. The bone tumor surgery device of claim 1, wherein the accommodation space is formed in a cylindrical shape.

8. The bone tumor surgery device of claim 7, wherein the accommodation container comprises a lower container forming a lower portion of the accommodation space and an upper container coupled to the lower container and forming an upper portion of the accommodation space.

9. The bone tumor surgery device of claim 1, wherein the accommodation container comprises a window formed to allow the accommodation space to be observed from the outside.

* * * * *